United States Patent [19]

Weinhold

[11] Patent Number: 4,598,621
[45] Date of Patent: Jul. 8, 1986

[54] MICROTOME HAVING A HANDWHEEL FOR DRIVING A SPECIMEN HOLDER

[75] Inventor: Helmut Weinhold, Ketsch, Fed. Rep. of Germany

[73] Assignee: Parke, Davis & Company, Morris Plains, N.J.

[21] Appl. No.: 706,827

[22] Filed: Feb. 28, 1985

[51] Int. Cl.⁴ ............................................. G01N 1/06
[52] U.S. Cl. .................................. 83/731; 74/89.22; 74/763; 74/810; 83/915.5
[58] Field of Search .............. 83/915.5, 707, 729, 83/731, 713; 74/810, 784, 792, 762, 763, 89.22

[56] References Cited

U.S. PATENT DOCUMENTS

| | | | |
|---|---|---|---|
| 316,594 | 1/1865 | Smith | 74/784 |
| 1,026,280 | 5/1912 | Ott | 83/915.5 |
| 3,212,379 | 10/1965 | McCormich et al. | 83/915.5 |
| 4,479,402 | 10/1984 | Reichel et al. | 83/915.5 |

FOREIGN PATENT DOCUMENTS 916849  1/1963  United Kingdom ............... 83/915.5

Primary Examiner—Frank T. Yost
Assistant Examiner—Hien H. Phan
Attorney, Agent, or Firm—Alan H. Spencer

[57] ABSTRACT

A microtome comprises a handwheel which can be rotated in two directions of rotation, and drive means for the purpose of driving a specimen holder, so that the specimen holder executes a cutting movement when the handwheel is rotated in one direction, and a resetting movement when the handwheel is rotated in the other direction. The cutting and resetting movements take place relative to a cutting knife. A reduction gearing arrangement enables the speed of the cutting movement to be reduced relative to the speed of the resetting movement without having to rotate the handwheel at a correspondingly lower rate. A catch enables the reduction gearing arrangement to be bridged so that the speed of the cutting movement and resetting movement are equal for any given rate of rotation of the handwheel.

17 Claims, 3 Drawing Figures

MICROTOME HAVING A HANDWHEEL FOR DRIVING A SPECIMEN HOLDER

BACKGROUND OF THE INVENTION

The invention relates to a microtome having a handwheel for driving a specimen holder.

Sliding microtomes may be provided with a drive handwheel on one of the sides of an oblong box-shaped housing, and with a specimen holder which executes a horizontal reciprocating movement inside the microtome housing when the handwheel is operated, that is to say, when it is rotated in one or the other of the two directions. The specimen holder moves relative to a cutting knife which is fastened to the housing. In such microtomes, the specimen holder commonly executes a cutting movement beneath the cutting knife when the handwheel, which is normally installed on the right-hand side of the microtome housing, is rotated in a clockwise direction. During this cutting movement, a thin section of a specimen held by the specimen holder is produced.

When the handwheel is rotated anticlockwise, the specimen holder executes a resetting movement, during which it is automatically displaced through a small distance, away from the cutting knife, so that the cutting knife does not scrape against the cut surface of the thin section specimen during the resetting movement, which would damage the cut surface or, possibly, result in wear of the cutting edge.

However, in known microtomes of this kind, the cutting movement and the resetting movement are both executed at the same speed. In order to carry out an accurate cut, it sometimes becomes necessary, in the case of hard specimens, to rotate the handwheel more slowly during the cutting movement than during the resetting movement. The resetting movement should be executed more rapidly in order to increase the efficiency of the thin section preparation work. However, in the case of known microtomes, the slow rotation of the handwheel during the cutting movement requires that the operators should possess adequate experience, and accordingly the quality of thin sections produced by means of a microtome of this type is also dependent on the experience of the operator.

SUMMARY OF THE INVENTION

It is an object of the present invention to provide an improved microtome, so that it becomes easier to operate, in that there is no need, during the cutting operation, to take the care which was previously needed with regard to the handwheel speed.

According to the invention there is provided a microtome comprising a cutting knife, a specimen holder movable relative to the cutting knife in first and second directions, a handwheel rotatable in opposite directions of rotation, drive means adapted to move the specimen holder in the first direction in response to rotation of the handwheel in one direction, and to move the specimen holder in the second direction in response to rotation of the handwheel in the other direction, and transmission means adapted to provide a ratio of the rate of movement of the specimen holder in the first direction, to the rate of rotation of the handwheel, which is less than the ratio of the rate of movement of the specimen holder in the second direction to the rate of rotation of the handwheel.

In this way the specimen holder can execute a slower movement in the first direction than in the second direction without having to rotate the handwheel at a correspondingly slower rate.

Advantageously the transmission means is operatively connected between the handwheel and the drive means.

Preferably the transmission means comprises reduction gearing means.

Typically the movement in the first direction corresponds to a cutting movement during which a thin section cut can be made, and the movement in the second direction corresponds to a resetting movement during which the specimen holder is returned to a position from where it can execute a further cutting movement. The cutting and resetting movements are preferably in a straight line relative to the cutting knife.

Preferably the reduction-gearing means comprises a sun wheel, two planet wheels, and an output wheel. The sun wheel may be mounted, by means of a first freewheel mechanism, on a central shaft on which the handwheel is rotatably mounted. The output wheel may be secured to a hollow shaft coaxial with the central shaft. The two planet wheels may be interconnected and mesh with the sun wheel and the output wheel respectively and may be rotatably mounted on a common planet wheel shaft provided on the handwheel.

Desirably a second freewheel mechanism is interposed between the hollow shaft and the handwheel. This second freewheel mechanism freewheeling counter to the direction in which the first freewheel mechanism freewheels.

The specimen holder can be driven from the hollow shaft by the drive means.

The parallel installation of the sun wheel and the output wheel, together with the planet wheels which mesh with them, enables the reduction-gearing means to be constructed in a very space-saving manner; for example, the reduction-gearing means may be accommodated in a handwheel possessing a comparatively small volume.

The two freewheel mechanisms with their freewheeling actions operative in opposite directions of rotation enable the handwheel to be directly connected to the drive means for the specimen holder in a 1:1 drive ratio in one of the directions of rotation. On rotating the handwheel in the opposite direction, a reduced transmission-ratio between the handwheel and the drive means is automatically achieved. The desired ratio may lie within an order of magnitude centered on 1:10 or may be lower, or higher, depending on the particular ratios which the numbers of teeth of the sun, output, and planet wheels bear to one another, as described in greater detail below.

The numbers of teeth possessed by the sun wheel, the two planet wheels, and the output wheel may be such that the product of the quotients specified hereafter is less than unity. These quotients are the results, respectively, of dividing the number of teeth on the sun wheel by the number of teeth on the output wheel, and of dividing the number of teeth on the planet wheel which meshes with the output wheel by the number of teeth on the planet wheel which meshes with the sun wheel. When this product is smaller than unity and the handwheel is installed on the right-hand side of the microtome housing and is rotated clockwise, the specimen holder can be arranged to move horizontally in the first direction to execute the cutting movement and make a cut. A microtome of this type is thus designed for right-handed persons.

It would, of course, also be possible to configure a microtome of this type especially for left-handed persons, that is to say with a handwheel installed on the left-hand side of the microtome housing. The specimen holder would then execute its horizontal cutting movement in the course of an anticlockwise rotation. This means that the above-mentioned product of the quotients of the numbers of teeth would have to exceed unity, which would be possible without difficulty, given appropriate selection of the numbers of teeth on the individual wheels of the planetary gear system.

However, when the microtome is arranged to make the cutting movement when the handwheel is rotated in the clockwise direction (i.e. for right-handed poeple), the output wheel may be provided with at least one tooth more than the sun wheel, and the planet wheel which meshes with the sun wheel may be provided with at least one tooth more than the planet wheel which meshes with the output wheel. By selecting the numbers of teeth in this way, it is possible without difficulty to accommodate a desired transmission-ratio of the order of magnitude of 1:10, or a lower or higher ratio, within a comparatively small space. The space saving is also assisted by the mounting of the planet wheels on the common planet wheel shaft; this shaft may be arranged horizontally.

Since, as has already been stated above, the reduction-gearing means provided in accordance with the invention require comparatively little space, the handwheel can be generally disk-shaped, having a faceplate and a rear portion, the faceplate, being rotatably mounted on the central shaft and the rear portion being mounted on the second freewheel mechanism; the planet wheel shaft may be mounted between the faceplate and the rear portion, and a handcrank may project from the faceplate. In this way, the design is very compact, and the gearwheels are effectively protected from external influence, thereby ensuring excellent operational reliability of the microtome according to the invention at all times.

The first freewheel mechanism can lock the sun wheel to the central shaft during rotation of the handwheel in a direction corresponding to the first direction of movement of the specimen holder, and allow the sun wheel to rotate freely during rotation of the handwheel in a direction corresponding to the second direction of movement of the specimen holder during which the handwheel is connected to the hollow shaft through the second freewheel mechanism.

As a result of locking the first freewheel mechanism in this manner, the sun wheel remains stationary on the central shaft which is in turn fixedly connected to the microtome housing. The reduction gearing, in the form of the planetary gear system, takes effect, and the drive means turns slowly in comparison with the handwheel; the drive means may be, for example, in the form of a chainwheel.

On rotating the handwheel in the direction corresponding to the second direction of movement of the specimen holder, the handwheel is connected directly to the drive means by means of the second freewheel mechanism. When the handwheel rotates in this direction, the output wheel rotates with it in the same direction, and the planet wheels accordingly also rotate. It is necessary that the sun wheel should also be able to rotate freely on the first freewheel mechanism, and in this direction of rotation this is permitted.

In this way, a very free-running handwheel is obtained, which can be driven in both directions of rotation, and it is possible for the horizontal motion of the specimen holder to be considerably slower during the cutting movement than during the resetting movement.

In a further development of the invention, the drive assembly is provided with means for bridging the transmission means whereby the specimen holder can move at the same speed upon rotation of the handwheel in either direction. This embodiment has the advantage of enabling the cutting movement to be carried out at the same speed as the resetting movement, when starting to cut a specimen, thus enabling the preliminary cuts to be carried out very quickly until a defined cutting area is reached. The means for bridging the transmission means may then be rendered inoperative, by means of simple manual actions, so that the transmission means can become effective.

The means for bridging the transmission means may comprise catch means including an actuating member movable between first and second positions, the actuating member in its first position locking the central shaft against rotation relative to the microtome housing, and the actuating member in its second position permitting the central shaft to rotate relative to the microtome housing, and being at the same time mechanically connected to the drive means.

When the actuating member is in its first position, the central shaft carrying the first freewheel mechanism is locked relative to the microtome housing, thus enabling this freewheel mechanism to operate in one of the directions of rotation of the handwheel to lock the sun wheel to the central shaft, and to allow the sun wheel to rotate freely in the other direction of rotation of the handwheel when the handwheel is connected directly to the drive means. In this way the specimen holder can be moved more slowly in one direction of rotation of the handwheel than in the other direction, as described above.

However, when the actuating member is in its second position, it enables the central shaft to rotate freely relative to the microtome housing, so that the first freewheel mechanism cannot become operative in either of the two directions in which the handwheel can rotate. At the same time, the handwheel is directly connected to the drive means, in both directions of rotation, so that the speed in which the drive means rotates corresponds precisely to that at which the handwheel rotates, and the specimen holder moves rapidly, whether during the cutting or resetting movement, on rotating the handwheel in either direction. This is an advantage, particularly while starting to cut a specimen.

The member for actuating the catch means may be a sleeve slidable along the handcrank and interacting with a lever inside the handwheel which lever is pivotable against spring means. By means of the lever the central shaft can be locked against, or freed for, rotation relative to the microtome housing. As a reult of installing the actuating member on the handcrank, it is simple to operate the actuating member at any time, using the same hand as for the handcrank, even while the handwheel is being rotated. In this way, the operation of the microtome according to the invention is made very easy. Designing the catch arrangement with a spring biassed level renders the handwheel construction compact, and results in a handwheel with excellent operating characteristics.

In the second position of the actuating member, the lever can connect the handwheel directly to the drive means, by means of a spring-mounted pin. This spring mounted pin may engage with the drive means when the handwheel is in virtually any position, thus preventing the occurrence of lost motion during the changeover from a reduced-ratio movement to the direct movement.

The central shaft can be hollow having a central shaft cavity, and a pin provided with a wedging surface can be axially slidably mounted in the cavity, between a spring and a further lever. The further lever is preferably secured to, or integral with, the lever described earlier. The central shaft may carry at least one locking pin directed away from the wedging surface and toward the microtome housing, whereby the or each locking pin can be wedged by the wedging surface between the housing and the central shaft to lock the central shaft against rotation.

Installing the pin inside the central shaft renders the construction very compact. It provides a good method for locking the central shaft relative to the microtome housing. It also provides a good method for unlocking the central shaft on appropriately actuating the catch means, so that the shaft can rotate freely relative to the microtome housing; as a result of this, the first freewheel mechanism remains inoperative on rotating the handwheel in either direction.

Through the use of the transmission means, it is possible to move the specimen holder considerably more slowly in the first direction than in the second direction while rotating the handwheel at a constant speed. As a result, it is unnecessary to rotate the handwheel so slowly and precisely during the cutting movement as when using the known microtomes, and it is possible to produce thin specimen-sections of very high quality with rapid handwheel rotation, as a consequence of the comparatively slow cutting movement. A further advantage is that, on rotating the handwheel in the opposite direction, the resetting movement of the specimen holder can automatically be effected by a direct transmission, and can consequently take place considerably more rapidly than the cutting movement. As a result of the feature whereby the reduction-gearing is automatically governed by the direction which the handwheel is rotated, the cutting movement can be discontinued at any position along the movement of the specimen holder, and changed to a resetting movement. In this manner, specimens from which thin sections are to be prepared, but which are of very widely differing sizes, can be cut very economically, because each slicing movement can be discontinued immediately behind the specimen from which the thin sections are being taken, and can be changed automatically into a rapid resetting movement by reversing the rotation directions of the handwheel.

BRIEF DESCRIPTION OF THE DRAWINGS

Further details, features and advantages will be apparent from the following description of illustrative embodiments of the invention which are repesented in the drawings, wherein.

DESCRIPTION OF THE PREFERRED EMBODIMENTS

Figure 1:
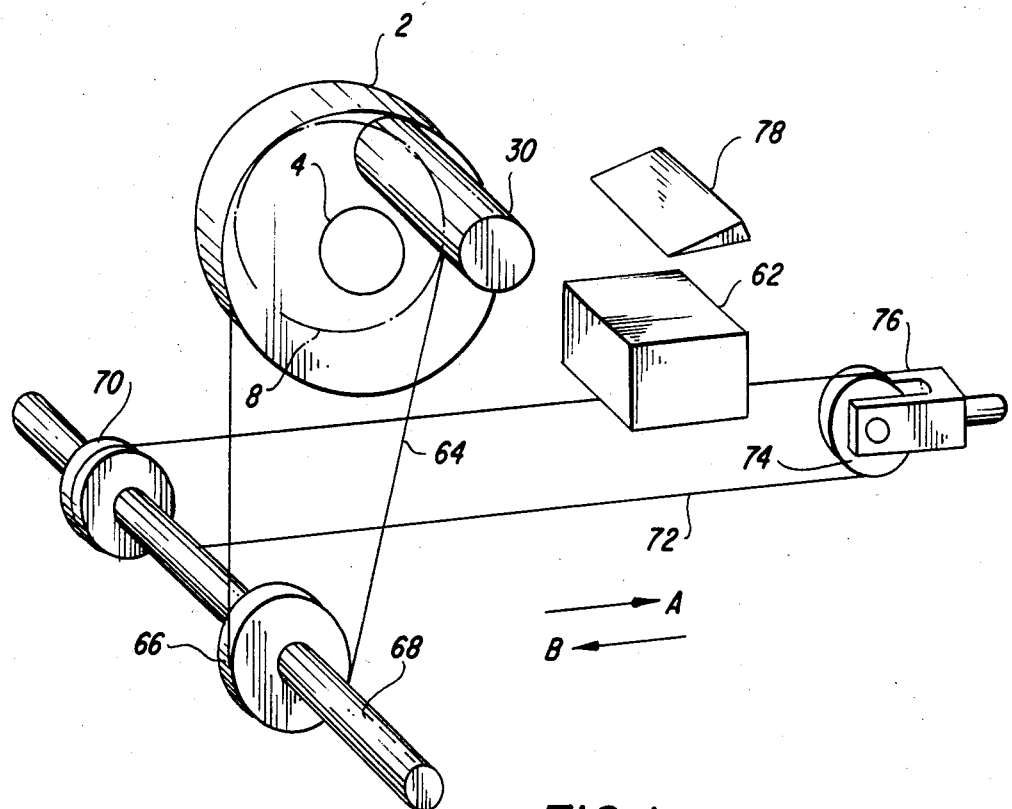
FIG. 1 is a schematic illustration of a microtome according to the invention.

In FIG. 1 a microtome 60 is shown schematically and in FIG. 1 the housing of the microtome is not shown in order to increase the clarity.

The microtome 60 includes a handwheel 2 mounted rotatably on a central shaft 4. A handcrank 30 is secured to the handwheel 2. Drive means for a specimen holder 62 is provided on the central shaft 4. The drive means comprises a chainwheel 8 around which an endless chain 64 is fitted. The endless chain 64 is also fitted around a chainwheel 66. The chainwheel 66 is mounted on a rotatable shaft 68, and a chainwheel 70 is also mounted on the shaft 68.

An endless chain 72 is fitted around the chainwheel 70, and the endless chain 72 is also fitted around a chainwheel 74. The chainwheel 74 is rotatable mounted to a mounting 76. The mounting 76 may be mounted on the microtome housing 6 (see FIGS. 2 and 3).

The specimen holder 62 is secured to the endless chain 72 and is movable relative to a cutting knife 78 which is mounted on the microtome housing 6.

When the handwheel 2 is rotated in one direction or in the opposite direction, the specimen holder 62 executes a cutting movement or a resetting movement respectively, relative to the cutting knife 78.

Figure 2:
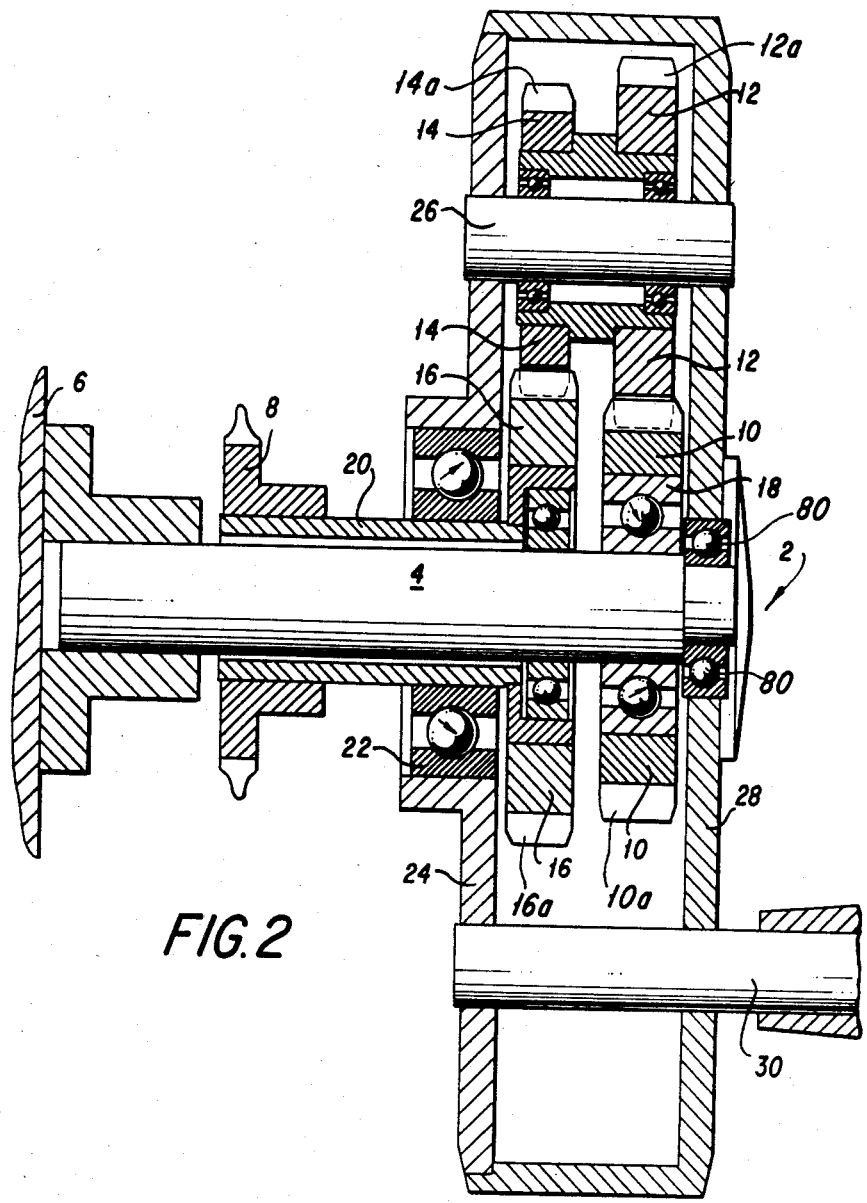
FIG. 2 shows a longitudinal section through part of one embodiment of a microtome according to the invention.

In FIG. 2 the central shaft 4 is shown rigidly 1 fastened to the microtome housing 6. FIG. 1 also shows reduction-gearing means which, when the handwheel 2 is rotated in one direction, enable the specimen holder 62 to execute a movement which is slower (that is to say a movement which has been geared down) than when the handwheel is rotated in the reverse direction.

The reduction-gearing means comprises a sun wheel 10, two planet wheels 12 and 14, and an output wheel 16. The sun wheel 10, the output wheel 16, and the planet wheels 12 and 14 are provided with teeth $10a$, $16a$, $12a$ and $14a$, respectively. The sun wheel 10 is mounted to a first freewheel mechanism 18 which is fastened to the central shaft 4. This freewheel mechanism 18 freewheels in a manner such that when the handwheel 2 is rotated clockwise, the sun wheel 10 is locked to the stationary central shaft 4 and likewise ceases to rotate. As can be seen from the Table which follows, the output wheel 16 rotates at a speed V which is given by the following expression, in which $n_s$ denotes the speed at which the handwheel is rotated in the clockwise direction:

$$V = +n_s \frac{(1 - z_a \cdot z_c)}{z_b \cdot z_d}$$

the output wheel likewise rotating clockwise. In the above expression:

$z_a$ denotes the number of teeth $10a$ on the sun wheel 10, $z_b$ denotes the number of teeth $12a$ on the planet wheel 12, $z_c$ denotes the number of teeth $14a$ on the planet wheel 14, and $z_d$ denotes the number of teeth 16a on the output wheel 16.

TABLE 1

| Gearwheel or handwheel | 10 | 12 | 14 | 16 | 2 |
|---|---|---|---|---|---|
| Gearwheels and handwheel locked; clockwise rotation at speed $n_s$ | $+n_s$ | $+n_s$ | $+n_s$ | $+n_s$ | $+n_s$ |
| Locking action Cancelled; handwheel stationary, sun wheel rotated anticlockwise | $+n_s$ | $+n_s \cdot \dfrac{z_a}{z_b}$ | $+n_s \cdot \dfrac{z_a}{z_b}$ | $-n_s \cdot \dfrac{z_a}{z_b} \cdot \dfrac{z_c}{z_d}$ | 0 |
| Super position of the two movements, i.e., summation | 0 | $n_s\left(1 + \dfrac{z_a}{z_b}\right)$ | $+n_s\left(1 + \dfrac{z_a}{z_b}\right)$ | $+n_s\left(1 - \dfrac{z_a}{z_b}\cdot\dfrac{z_c}{z_d}\right)$ | $+n_s$ |

It is clear from the last line of the Table, that the output wheel 16 rotates at a speed $$n_s \frac{(1 - z_a \cdot z_c)}{z_b \cdot z_d}$$

on rotating the handwheel clockwise at the speed $n_s$. When the quotient in this term is smaller than unity, it follows that the bracketed value is greater than zero, and that the output wheel 16 likewise rotates in the clockwise direction.

For this purpose, the output wheel 16 has at least one tooth more than the sun wheel 10, and the planet wheel 12 has at least one tooth more than the planet wheel 14. For example, the number of teeth may be $z_a = 28$, $z_b = 23$, $z_c = 22$, and $z_d = 29$, so that the ratio of the speed of the output wheel 16 to that of the handwheel 2 is according to the expression $$n_s\left(1 - \frac{z_a \cdot z_c}{z_b \cdot z_d}\right) : n_s$$

$$= \left(1 - \frac{28 \cdot 22}{23 \cdot 29}\right) : 1$$

$$= 0.0765 : 1$$

$$= 1 : 13$$

The above reduction ratio means that while the handwheel rotates 13 times, the output wheel 16 rotates once about a hollow shaft 20 to which the chainwheel 8 is fastened. The output wheel 16 is also fastened to the hollow shaft 20; the output wheel 16 is mounted concentrically with the hollow shaft 20. The hollow shaft 20 is mounted coaxially on the central shaft 4, and can rotate relative thereto.

A second freewheel mechanism 22 is likewise mounted on the hollow shaft 20, freewheeling counter to the direction in which the first freewheel mechanism 18 freewheels. The handwheel 2 is mounted, by means of a rear portion 24, on the second freewheel mechanism 22. If, therefore, the handwheel 2 is rotated anticlockwise, the second freewheel mechanism 22 is locked, and the rotation of the handwheel 2 is transmitted directly by the second freewheel mechanism 22 directly to the hollow shaft 20, that is to say without any gearing-down, and thence to the chainwheel 8.

The planet wheels 12 and 14 are parallel to one another and mesh respectively with the sun wheel 10 and with the output wheel 16; the output wheel 16 is mounted coaxially with the sun wheel 10. The planet wheels 12 and 14 are rotatably mounted on a common planet wheel shaft 26 which is parallel to the central shaft 4.

The handwheel 2 is generally disk-shaped, having a faceplate 28 secured to the rear portion 24. The faceplate 28 is provided with bearings 80 which permit the faceplate to be rotatably mounted on the central shaft 4. The planet wheel shaft 26 is installed between the faceplate 28 and the rear portion 24 of the handwheel 2. The handcrank 30 projects from the faceplate 28 of the handwheel 2.

The first freewheel mechanism 18 locks the sun wheel 10 to the stationary central shaft 4 during clockwise rotation of the handwheel 2. The planet wheel 12 meshes with the sun wheel 10, and at the same time, being mounted on the planet wheel shaft 26 between the faceplate 28 and the rear portion 24, the second planet wheel 14 rotates with it, at the same speed (see the preceding Table). Rotation of the second planet wheel 14 causes rotation of the output wheel 16, geared-down correspondingly. Since the output wheel 16 is rigidly connected, by means of the hollow shaft 20, to the chain wheel 8, the clockwise rotation of the handwheel 2 is transmitted, geared down, to the chainwheel 8. Since the second freewheel mechanism 22 is free during clockwise rotation of the handwheel 2, the second freewheel mechanism presents absolutely no hindrance to the clockwise rotation of the handwheel.

During anticlockwise rotation of the handwheel 2, the second freewheel mechanism 22 is locked, so that the rotation of the handwheel is transmitted, by the second freewheel mechanism, directly to the hollow shaft 20, and thence to the chainwheel 8. During this anticlockwise rotation, the first freewheel mechanism 18 is unlocked, so that corresponding rotation of the output wheel 16 via the planet wheels 14 and 12 back to the sun wheel 10 is readily possible.

By this means, it is possible to drive the handwheel 2, by means of its handcrank 30, in either direction of rotation without any hindrance.

In this regard, it is particularly advantageous that changing the rotation direction from clockwise to anticlockwise is automatically accompanied by a transition from the geared-down drive to a direct drive, thus enabling the cutting movement to be carried out slowly and accurately, and enabling the movement for resetting the specimen holder to be accomplished very much more rapidly.

The specimen holder 62 is horizontally movable, from an initial position, in the first direction, during which movement the speciment holder executes the cutting movement relative to the cutting knife 78 thus enabling a thin section cut of a specimen (not shown) held by the specimen holder to be made. This direction of movement is indicated by arrow A.

The specimen holder 62 is horizontally movable in a second direction during which movement the specimen holder executes the resetting movement relative to the cutting knife 78. During this movement the specimen holder 62 moves back to the initial position from where a further cutting movement can be executed.

The speed of the cutting and resetting movements depends upon the speed at which the handwheel 2 is rotated. However, for a constant speed of rotation of the handwheel in each direction, the speed of the cutting movement is slower than the speed of the resetting movement, due to the reduction gearing means.

Figure 3:
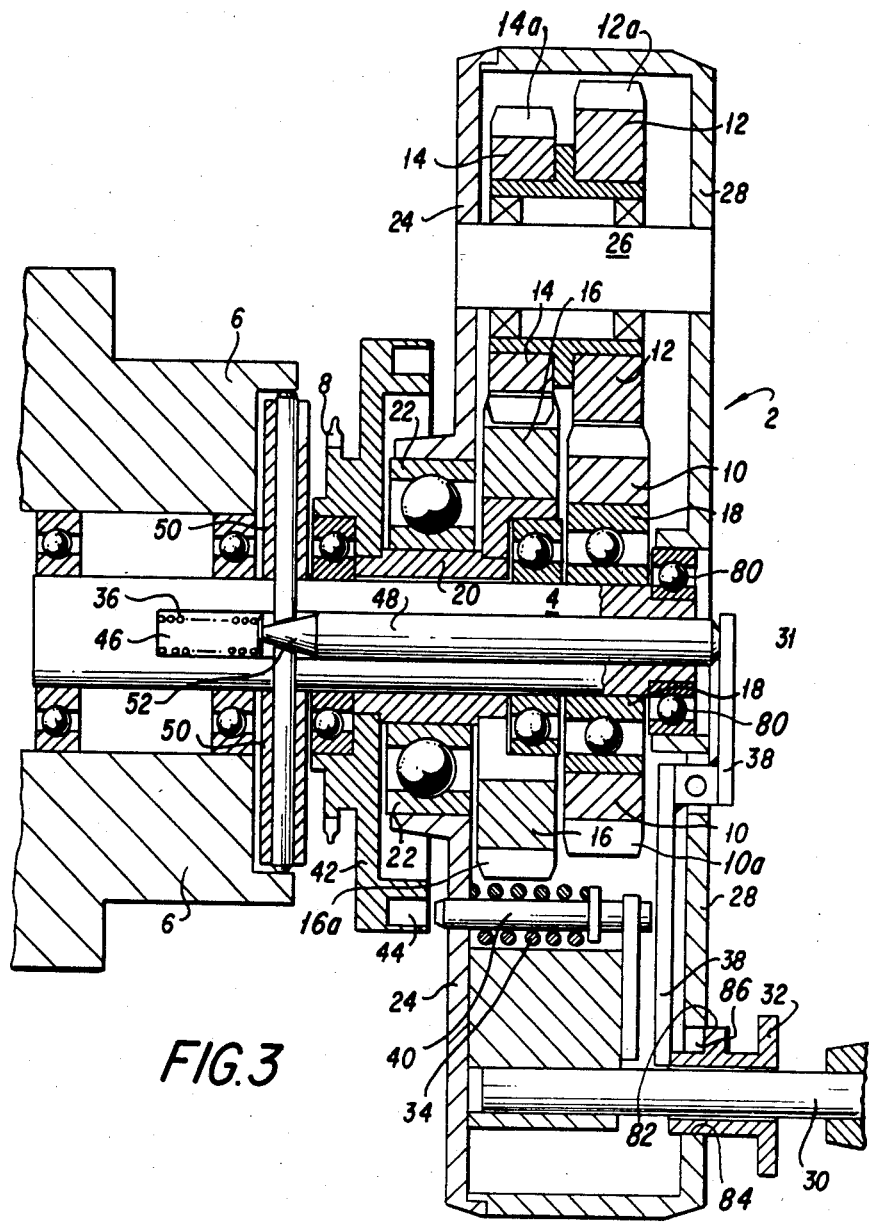
FIG. 3 shows a longitudinal section through part of another embodiment of a microtome according to the invention.

FIG. 3 shows a handwheel 2, corresponding to the handwheel 2 shown in FIG. 2, and like parts have been designated with like reference numerals.

The central shaft 4 is capable not only of being rigidly connected to the microtome housing 6, but is also capable of being rotated relative thereto. For this purpose, catch means 31 is employed, including an actuating member 32 which can be shifted between first and second positions. In the first position of the actuating member 32, the central shaft 4 is locked, so that it cannot turn relative to the microtome housing 6, with the result that the handwheel 2 has the same action as has been described by reference to FIG. 2.

In the second position of the actuating member 32, the central shaft 4 is rotatable relative to the microtome housing 6. In this second position the actuating member 32 is at the same time mechanically connected to the chainwheel 8, the connection being rigid. The actuating member 32 comprises a sleeve which can be slid along the handcrank 30 through an aperture 84 in the front plate 28. The aperture 84 is dimensioned so that it is just large enough to receive the sleeve. The sleeve of the actuating member 32 interacts with a lever 38 carried inside the handwheel 2; the lever 38 is mounted in a manner such that it can pivot against spring means, 34 and 36. By means of the lever 38 the central shaft 4 can be locked or allowed to rotate freely relative to the microtome housing 6.

A projection 82 is provided on the sleeve of the actuating member 32. When the actuating member 32 is moved from one position to the other, the projection 82 can be aligned with a recess 86 which communicates with the aperture 84, and can be pushed through the recess 86. The recess 86 is dimensioned so that it is just large enough to receive the projection 82. When the actuating member 32 has been moved to the second position the sleeve and projection 82 can be rotated relative to the face plate 28 in order to place the projection out of alignment with the recess 86. In this way the projection 82 engages the inner surface of the face plate 28 and serves to hold the actuating member 32 in the second position. In order to move the actuating member 32 to the first position the pojection 82 must first be realigned with the recess 86.

In the second position of the actuating member 32, the lever 38 connects the handwheel 2, to a plate 42, which is rigidly secured to the chainwheel 8, by means of a spring-mounted pin 40. For this purpose, the plate 42 is provided with a plurality of recesses 44 located side-by-side around its periphery. On moving the actuating member 32 to the second position, the pin 40 latches into one of the recesses 44 against the force of spring means 34, so that rotation of the handwheel 2, in either direction, is transmitted directly to the chainwheel 8 by the pin 40. When the lever 38 is in this position, the spring means 36 presses a pin 48 outwardly, the pin 48 being axially slidably mounted in central cavity 46 of the central shaft 4. Locking pins 50, which are provided between a wedging surface 52 of the pin 48 and the microtome housing 6, are thereby released, that is to say are unlocked, and the central shaft 4 can rotate freely. Because the central shaft 4 is rotating freely, the first freewheel mechanism 18 cannot become operative in either of the directions in which the handwheel 2 can rotate, so that rotation of the handwheel 2 in either direction is transmitted to the chainwheel 8 directly, that is to say in a 1:1 ratio.

When the actuating member 32 is in the first position, the pin 48 is pressed into the hollow central shaft 4, against the spring means 36. At the same time, the locking pins 50 are driven radially apart, along the wedging surface 52, thus wedging them between the wedging surface of the pin 48 and the microtome housing 6. In this wedged position, the central shaft 4 is thus locked to the microtome housing 6, and the reduction-gearing means can become operative, as has already been described with reference to FIG. 2.

With the embodiment of the drive assembly 2 represented in FIG. 3, provided with catch means 31, it is thus possible, when the actuating member 32 is in the second of its positions on the handcrank 30, to drive the chainwheel 8 and hence the specimen holder in a 1:1 ratio on rotating the handwheel 2 in either direction, namely to effect horizontal movement of the specimen holder 62 at one and the same speed during both the cutting movement and the resetting movement. This is an advantage, particularly when starting to cut a sample from which thin sections are to be taken.

When the actuating member 32 is in the first position, it is possible in a very simple manner to lock the central shaft 4 relative to the microtome housing 6. At the same time, the freewheel mechanisms 18 and 22 and the planetary-gear system become operative in the manner described with reference to FIG. 2. That is to say, on rotating the handwheel 2 in one direction, the speed of rotation is geared down, so that if the handwheel 2 is rotated at equal speeds, the cutting movement is effected considerably more slowly than the resetting movement.

At the same time, it is also particularly advantageous that the member 32 for actuating the catch means 31 can be operated at any time and when the specimen holder is in any position. It is expedient that the member 32 can be operated according to the length of the specimen which is to be cut.

Electromechanical and/or mechanical means can be coupled to the movement of the specimen holder, these means triggering both the feed mechanism which sets the thickness of the cut to be made, and the reverse stroke of the specimen holder which is automatically initiated at the specimen-holder reversal points. For example, the electromechanical or mechanical means can move the specimen holder vertically away from the cutting knife before executing the resetting movement in order to avoid damage to the cutting knife or specimen. In this manner there is provided a microtome which is both very simple and easy to handle, and by means of which very precise work can be carried out at any time, under optimum conditions.

We claim:

1. A microtome comprising:
    a cutting knife,
    a specimen holder movable relative to the cutting knife in first and second directions,
    a handwheel rotatable in opposite directions of rotation,
    drive means adapted to move the specimen holder in the first direction in response to rotation of the handwheel in one direction, and to move the specimen holder in the second direction in response to rotation of the handwheel in the other direction,
    and transmission means adapted to provide a ratio of the rate of movement of the specimen holder in the first direction to the rate of rotation of the handwheel, which is less than the ratio of the rate of movement of the specimen holder in the second direction to the rate of rotation of the handwheel.

2. A microtome as claimed in claim 1 wherein the transmission means comprises reduction gearing means.

3. A microtome as claimed in claim 1 wherein the transmission means is operatively connected between the drive means and the handwheel.

4. A microtome as claimed in claim 1 wherein the transmission means is disposed within the handwheel.

5. A microtome as claimed in claim 2, further comprising a central shaft on which the handwheel is rotatably mounted, a hollow shaft coaxial with the central shaft, a first freewheel mechanism, a second freewheel mechanism, and a planet wheel shaft on the handwheel.

6. A microtome as claimed in claim 5 wherein the reduction-gearing means comprises a sun wheel, two planet wheels, and an output wheel, the sun wheel being mounted, by means of the first freewheel mechanism, on the central shaft, the output wheel being secured to the hollow shaft, and the two planet wheels being interconnected and meshing with the sun wheel and the output wheel respectively and being rotatably mounted on the planet wheel shaft.

7. A microtome as claimed in claim 6 wherein the second freewheel mechanism is disposed between the hollow shaft and the handwheel, and the second freewheel mechanism freewheels counter to the direction in which the first freewheel mechanism freewheels.

8. A microtome as claimed in claim 5 and wherein the specimen holder is driven from the hollow shaft.

9. A microtome as claimed in claim 6, wherein the sun wheel, the two planet wheels, and the output wheel each possesses a respective number of teeth such that the product of the quotients specified hereafter is less than unity, these quotients being the results, respectively, of dividing the number of teeth on the sun wheel by the number of teeth on the output wheel, and of dividing the number of teeth on the planet wheel which meshes with the output wheel by the number of teeth on the planet wheel which meshes with the sun wheel.

10. A microtome as claimed in claim 9, wherein the output wheel has at least one tooth more than the sun wheel, and wherein the planet wheel which meshes with the sun wheel has at least one tooth more than the planet wheel which meshes with the output wheel.

11. A microtome as claimed in claim 7, wherein the handwheel is generally disk-shaped, having a faceplate, a rear portion, and a handcrank projecting from the faceplate, the faceplate is rotatably mounted on the central shaft, the rear portion is mounted on the second freewheel mechanism, and the planet wheel shaft is mounted between the faceplate and the rear portion.

12. A microtome as claimed in claim 7, wherein the first freewheel mechanism locks the sun wheel to the central shaft during rotation of the handwheel in the direction corresponding to the movement of the specimen holder in the first direction, and allows the sun wheel to rotate freely during rotation of the handwheel in the direction corresponding to the movement of the specimen holder in the second direction, and the handwheel is connected to the hollow shaft through the second freewheel mechanism during rotation of the handwheel in the direction corresponding to movement of the specimen holder in the second direction.

13. A microtome as claimed in claim 1, wherein means is provided for bridging the transmission means to provide a ratio of the rate of movement of the specimen holder in the first direction to the rate of rotation of the handwheel which is substantially equal to the ratio of the rate of movement of the specimen holder in the second direction to the rate of rotation of the handwheel.

14. A microtome as claimed in claim 13, wherein the means for bridging the transmission means comprises catch means including an actuating member movable between first and second positions, the actuating member in its first position locking the central shaft against rotation relative to a microtome housing, and the actuating member in its second position permitting the central shaft to rotate relative to the microtome housing and being at the same time mechanically connected to drive means.

15. A microtome as claimed in claim 14, further comprising a handcrank on the handwheel, a lever, disposed within the handwheel, and spring means against which the lever is pivotable, and wherein the actuating member comprises a sleeve slidable along the handcrank and interacting with the lever, by means of which lever the central shaft can be locked against, or freed for, rotation.

16. A microtome as claimed in claim 15, further comprising a spring-mounted pin, and wherein in the second position of the actuating member the lever connects the handwheel directly to the drive means, by means of the spring-mounted pin.

17. A microtome as claimed in claim 13, wherein the central shaft is hollow having a central shaft cavity, and a pin provided with a wedging surface is axially slidably mounted in the cavity between a spring and an actuating lever, and the central shaft carries at least one locking pin directed away from the wedging surface and towards a microtome housing, whereby the or each locking pin can be wedged by the wedging surface between the housing and the central shaft to lock the central shaft against rotation.

* * * * *